(12) United States Patent
Buelow et al.

(10) Patent No.: US 12,243,633 B2
(45) Date of Patent: Mar. 4, 2025

(54) REAL-TIME DIGITAL IMAGING AND COMMUNICATION IN MEDICINE (DICOM) LABEL CHECKER

(71) Applicant: KONINKLIJKE PHILIPS N.V., Eindhoven (NL)

(72) Inventors: Thomas Buelow, Grosshansdorf (DE); Tanja Nordhoff, Hamburg (DE); Tim Philipp Harder, Ahrensburg (DE); Hrishikesh Narayanrao Deshpande, Hamburg (DE); Olga Starobinets, Newton, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 921 days.

(21) Appl. No.: 17/231,043

(22) Filed: Apr. 15, 2021

(65) Prior Publication Data

US 2021/0366592 A1 Nov. 25, 2021

Related U.S. Application Data

(60) Provisional application No. 62/704,653, filed on May 20, 2020.

(51) Int. Cl.
*G16H 30/20* (2018.01)
*G06T 7/00* (2017.01)
*G16H 30/40* (2018.01)

(52) U.S. Cl.
CPC ........... *G16H 30/20* (2018.01); *G06T 7/0012* (2013.01); *G16H 30/40* (2018.01); *G06T 2207/20081* (2013.01)

(58) Field of Classification Search
CPC ........ G16H 30/20; G16H 30/40; G16H 50/20; G06T 7/0012; G06T 2207/20081
See application file for complete search history.

(56) References Cited

U.S. PATENT DOCUMENTS

| 10,650,267 B2 * | 5/2020 | Yoshida | G16H 30/40 |
| 10,824,908 B1 * | 11/2020 | Park | G16H 30/40 |
| 2009/0089742 A1 | 4/2009 | Nagulu | |
| 2016/0062956 A1 | 3/2016 | Gotman | |
| 2016/0092748 A1 * | 3/2016 | Koktava | G06T 7/0012 382/128 |
| 2016/0328517 A1 * | 11/2016 | Deng | G16H 30/40 |
| 2016/0364539 A1 * | 12/2016 | Reicher | G16H 20/10 |
| 2017/0265836 A1 * | 9/2017 | Laor | A61B 6/582 |
| 2018/0060534 A1 * | 3/2018 | Reicher | G16H 30/20 |
| 2019/0313992 A1 | 10/2019 | Buelow | |

(Continued)

*Primary Examiner* — Ping Y Hsieh
*Assistant Examiner* — Jose M Torres
(74) *Attorney, Agent, or Firm* — Larry Liberchuk

(57) ABSTRACT

An apparatus (1), for use in conjunction with a medical imaging device (2) having an imaging device controller (4) that displays a graphical user interface (GUI) (8) including a preview image viewport (9), includes at least one electronic processor (20) programmed to: perform an image analysis (38) on a preview image displayed in the preview image viewport to generate preview-derived image label information; extract GUI-derived image label information from the GUI excluding the preview image displayed in the preview image viewport; and output an alert (30) when the preview-derived image label information and the GUI-derived image label information are not consistent.

17 Claims, 3 Drawing Sheets

(56) References Cited

U.S. PATENT DOCUMENTS

| | | | |
|---|---|---|---|
| 2019/0333625 A1* | 10/2019 | Barkan | G16H 50/70 |
| 2020/0258215 A1* | 8/2020 | Kashyap | G06V 10/82 |
| 2021/0109829 A1* | 4/2021 | Lee | G16H 30/40 |
| 2021/0216822 A1* | 7/2021 | Paik | G16H 15/00 |
| 2022/0101984 A1* | 3/2022 | Park | G06V 10/70 |
| 2022/0301690 A1* | 9/2022 | Maack | G16H 30/40 |

* cited by examiner

REAL-TIME DIGITAL IMAGING AND COMMUNICATION IN MEDICINE (DICOM) LABEL CHECKER

CROSS REFERENCE TO RELATED APPLICATIONS

This application claims the benefit of U.S. Provisional Patent Application No. 62/704,653 filed May 20, 2020. This application is hereby incorporated by reference herein.

FIELD

The following relates generally to the imaging arts, image storage, communication, and archiving arts, image label determination arts, real-time imaging acquisition feedback arts, and related arts.

BACKGROUND

The clinical images acquired during medical imaging examinations are typically stored in a Picture Archiving and Communication System (PACS) or other medical imaging database. The images stored in the PACS are tagged with image label information (also referred to as image tags), typically in the form of image metadata complying with the Digital Imaging and Communications in Medicine (DICOM) standard for medical imaging information. The image labels or tags provide information ranging from patient information to image information, for example stored as DICOM header fields such as ViewPosition, ImageLaterality, PatientOrientation, BodyPartExamined, or so forth.

Diagnostic interpretation of radiologic images often includes the review of images acquired in relevant prior exams for comparison. The reviewed prior exams may include prior imaging examinations of the current patient, and/or prior imaging examinations of other patients with similarity to the current patient. Relevant exams can be selected based on information contained in the DICOM header of a clinical image, such as laterality, view-position, or body-part. However, a problem can arise in that some images may contain faulty DICOM header information, which can lead to the display of unrelated, irrelevant images, and perhaps more importantly can lead to the exclusion of relevant prior images. Furthermore, while a skilled radiologist can usually be expected to recognize an erroneous image tag relating to the image content upon seeing the actual image (for example, the radiologist should recognize an erroneous BodyPartExamined or PatientOrientation tag upon seeing the actual image), erroneous image tags can lead to delays in performing the reading of an imaging examination, and have to potential to lead to misinterpretation of images causing an incorrect diagnosis, among other issues.

Still further, any inconsistency between an image and a corresponding image tag likely reflects an underlying issue in performing the medical imaging examination. For example, if the image label information indicates a lateral image acquisition while the actual image is a frontal image, then there are two possible errors. First, the imaging technician may have erroneously set up the imaging device to perform a lateral image acquisition but correctly acquired a frontal image in accord with the examination order. In this case, the correct image is stored at the PACS, but with an erroneous lateral image tag. The erroneous tag may initially confuse the radiologist and result in a longer reading time, and also may result in a subsequent image search on frontal images failing to locate the erroneously labeled frontal image (or, conversely, a search on lateral images returning the erroneously labeled frontal image). The alternative possible cause for the label/image inconsistency is even more problematic: the imaging technician may have correctly set up the imaging device to perform a lateral image acquisition in accord with the examination order, but erroneously acquired a frontal image. In this latter case, not only will the frontal image be mislabeled as a lateral image, but the erroneously acquired frontal image may be of limited or no medical value, if the clinician requires a lateral image in order to perform the medical diagnosis or evaluation. Hence, the imaging examination may need to be repeated.

The following discloses certain improvements to overcome these problems and others.

SUMMARY

In one aspect, an apparatus, for use in conjunction with a medical imaging device having an imaging device controller that displays a graphical user interface (GUI) including a preview image viewport, includes at least one electronic processor programmed to: perform an image analysis on a preview image displayed in the preview image viewport to generate preview-derived image label information; extract GUI-derived image label information from the GUI excluding the preview image displayed in the preview image viewport; and output an alert when the preview-derived image label information and the GUI-derived image label information are not consistent.

In another aspect, an apparatus, for use in conjunction with a medical imaging device having an imaging device controller that displays a GUI including a preview image viewport, includes: at least one display device separate from the imaging device controller; a video cable splitter operatively connected with the imaging device controller; and at least one electronic processor programmed to: receive a video feed of the GUI displayed on the imaging device controller via the video cable splitter; extract a preview image displayed in the preview image viewport from the live video feed of the GUI; perform an image analysis on the extracted preview image to generate preview-derived image label information; extract GUI-derived image label information from the live video feed of the GUI, the GUI-derived image label information including one or more of body part information, anatomical information of a body part, and textual information; and output an alert when the preview-derived image label information and the GUI-derived image label information are not consistent on the display device that is separate from the imaging device controller.

In another aspect, a method for providing real-time checking of label information includes: receiving a video feed of a GUI displayed on an imaging device controller; extracting a preview image displayed in a preview image viewport of the GUI from the live video feed; performing an image analysis on the extracted preview image to generate preview-derived image label information; detecting a user input to the GUI captured by the live video feed of the GUI; extracting at least a portion of the GUI-derived image label information from the live video feed of the GUI based on the detected user input; and outputting an alert when the preview-derived image label information and the GUI-derived image label information are not consistent.

One advantage resides in providing a check of image label information (e.g., information destined to be used to generate DICOM image header content) in real time.

Another advantage resides in providing a system to provide a process for checking image label information in real time prior to transferring clinical images to the PACS or other medical imaging database, and without configuring the system for different imaging modalities and models.

Another advantage resides in providing a DICOM label checking on acquired images of a patient before the patient moves to a post-imaging procedure in a workflow.

Another advantage resides in providing a DICOM label checking process on acquired images of a patient without modifying the imaging device controller to do so.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
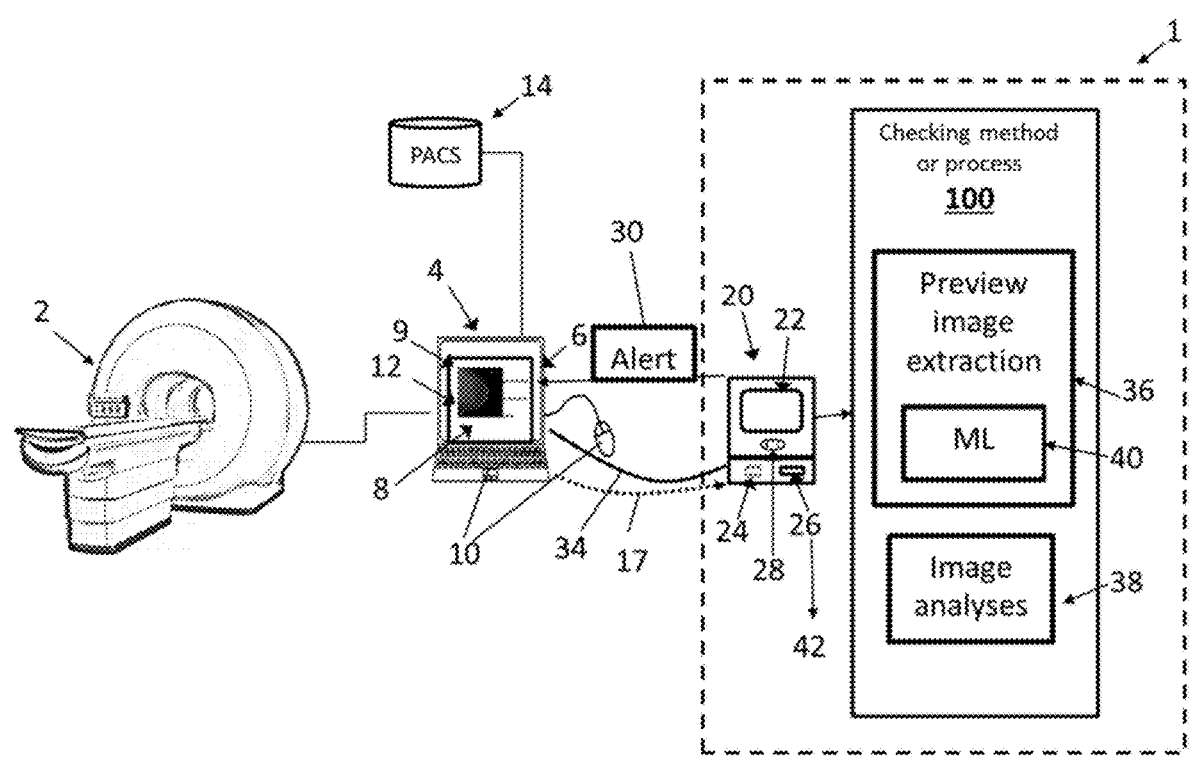
FIG. 1 diagrammatically illustrates an illustrative apparatus for checking information in acquired images in accordance with the present disclosure.

As previously noted, image label errors can create various problems. Hence, it would be useful to ensure accuracy of the image label information prior to the medical images being finalized, labeled, and stored to the PACS or other clinical images database. One approach would be to implement a quality feedback mechanism directly into an image acquisition console. This allows for immediate feedback at the console right after image acquisition. Unfortunately, a change to the software of existing consoles would require costly recertification of the imaging system, which may not be a viable approach. Moreover, comprehensive implementation of this approach in a radiology laboratory would require upgrading the imaging device controller for each and every imaging device at the lab, which may be problematic if the radiology laboratory employs various makes and models of imaging devices.

In order to provide a solution that is vendor agnostic, in a conventional set-up, the earliest possible time to access the images for image label checking is after the medical imaging examination is completed and sent off to subsequent DICOM nodes (usually a PACS database). However, by the time this occurs, the patient is usually in the post-examination phase. If the inconsistency between an image and its image label is due to the wrong image being acquired, then it may be difficult or impossible to recall the patient in order to acquire the correct image.

In medical imaging, the acquired clinical images are labeled with a large amount of information, including but not limited to patient identification (ID), imaging modality, examined body part, view position, patient orientation, image laterality, and so forth. The data for these fields may be directly entered, or more commonly selected via graphical user interface (GUI) operations. For example, the technologist may navigate via the GUI to select chest image acquisition, which brings up a chest imaging-specific configuration display, and then may select lateral orientation, and perhaps other settings, finally arriving at a GUI display showing a window for presenting the lateral chest image preview as it is acquired. The imaging controller collects various labeling information based on the GUI navigation, and tags the final clinical image with this information as it is sent to the PACS. The labeling metadata is tagged to the image using the industry-wide standard DICOM format.

A potential problem can arise if the technologist navigates to the wrong image acquisition screen. In the above example, such an error could arise if the technologist erroneously selects a frontal orientation rather than the intended lateral orientation (e.g., per the imaging examination order), yet correctly positions the patient to acquire a lateral image. The screen will still display the acquired lateral preview image, and the resulting clinical image will be a lateral image but will be erroneously tagged with DICOM data indicating it is a frontal orientation image. The later-reviewing radiologist will likely immediately recognize the erroneous DICOM header since the image will be recognized as a lateral image in spite of the "frontal" DICOM label. However, the erroneous DICOM label could have adverse effects such as adversely impacting image searches reliant upon DICOM labels. Conversely, the technologist may navigate to the correct image acquisition screen, but then acquire an incorrect image. As an example of this possibility, the technologist may correctly select the frontal orientation (e.g., per the imaging examination order) but then erroneously acquire a lateral preview image. In this case, if the error is not timely detected then the imaging examination might need to be redone at a later date.

The following discloses a real-time method for automatically checking DICOM labels by comparing image label information obtained by image analysis of an extracted preview image displayed in the preview image viewport with GUI-derived image label information from the GUI (excluding the preview image displayed in the preview image viewport). In some embodiments, such a check can be done at the imaging controller, which has direct access to both the preview image displayed in the preview image viewport and information entered into and displayed by the GUI. However, this approach requires modifying the imaging controller, which in turn might require regulatory recertification of the controller. Furthermore, this approach cannot be implemented in a vendor-agnostic manner, and requires updating the software of each make and model of imaging controller.

Accordingly, the illustrative embodiment taps off the imaging controller display video feed, for example using a DVI splitter, in order to monitor the GUI display. As the technologist navigates the GUI, data entry and GUI navigation are monitored to detect DICOM labels being generated by the GUI navigation and/or data entry. This can be done by OCR, and/or by matching with imaging controller GUI user dialog window templates. (In the alternative embodiments implemented in the imaging device controller, the GUI navigation and/or data entry is directly available at the controller). Some image label information may be auto populated into the GUI dialogs without user-supplied data entry, for example by reading the imaging examination order obtained from the Radiology Information System (RIS), and again these DICOM labels can be detected by OCR and/or template matching. (Again, in alternative embodiments implemented in the imaging device controller, the auto-populated image label information is directly available at the controller).

When the preview image is acquired, it is recognized in, and extracted from, the tapped video feed. (Again, in alternative embodiments implemented in the imaging device controller, the preview image displayed in the preview image viewport is directly available at the controller). Machine learning (ML) algorithms, pattern matching, or other image analyses are performed on the preview image to determine correct DICOM labels for the preview image. This preview image-derived image label information is compared against the GUI interaction-derived image label information, and any discrepancies are reported as alerts notifying the technologist of the discrepancy. In the illustrative embodiments, the output can be provided on a separate display (e.g. separate notebook computer), to avoid modifying the imaging controller (and consequent need for recertification) and to enable the system to be vendor-agnostic. (In alternative embodiments implemented in the imaging device controller, the output can, for example, be displayed in a pop-up window shown on the display of the imaging device controller).

With reference to FIG. 1, an illustrative apparatus 1 providing immediate DICOM image label checking processes during an imaging examination is shown. The apparatus 1 is used in conjunction with an image acquisition device 2, which can be (by way of nonlimiting illustrative examples) a Magnetic Resonance (MR) image acquisition device, a Computed Tomography (CT) image acquisition device; a positron emission tomography (PET) image acquisition device; a single photon emission computed tomography (SPECT) image acquisition device; an X-ray image acquisition device; an ultrasound (US) image acquisition device; a mammography device, or a medical imaging device of another modality. The imaging device 2 may also be a hybrid imaging device such as a PET/CT or SPECT/CT imaging system. The medical imaging device 2 is controlled via an imaging device controller 4, which includes a display 6 on which a graphical user interface (GUI) 8 is presented to a user (e.g., an imaging technician), and one or more user input devices 10 (e.g. keyboard, trackpad, mouse, et cetera) via which the user interacts sets up and controls the medical imaging device 2 to acquire clinical images. The apparatus 1 also includes a preview image viewport 9 displayed via the GUI 8.

In the process of setting up to acquire the clinical images, the GUI 8 is operated to cause the medical imaging device 2 to acquire and display a preview image 12 on the preview image viewport 9. The preview image 12 is usually acquired and displayed at a lower resolution than the clinical image(s) that are subsequently acquired, but is sufficient for the user to verify that the correct anatomy is being imaged, that the anatomy is correctly positioned, is of a usefully large size (but not too large) in the image, and so forth. When the user is satisfied, based on the preview image 12 and other information, that the imaging device 2 is correctly set up to acquire the desired clinical image(s), the user operates the GUI 8 to initiate the clinical imaging, reviews the acquired clinical images on the display 6, and ultimately stores the final clinical images along with image labels created from image label information generated by the GUI navigation and/or data entry (or, in some cases, auto populated into the GUI dialogs from the RIS or other linked database).

FIG. 1 also shows the apparatus 1 for providing immediate checking of image label information for the user (e.g. imaging technician) during the imaging examination. The apparatus 1 is preferably, although not necessarily, a separate device from the imaging device controller 4. For example, the apparatus 1 may comprise a computer or other electronic processing device 20 embodied as a notebook computer, tablet computer, a Raspberry Pi or other single-board computer, or so forth) and includes a display 22, an electronic processor (e.g. one or more microprocessors) 24 and a non-transitory storage medium 26. (Note, the electronic processor 24 and a non-transitory storage medium 26 are diagrammatically shown in FIG. 1, but are typically internal components, e.g. housed inside the housing of the computer 20). The display 22 presents one or more alerts 30 when a possible inconsistency with DICOM labels is detected. Optionally, the apparatus 1 further includes a loudspeaker 28, e.g. mounted in or on the computer 20, for providing an audible indication when an alert 30 is presented.

While the apparatus 1 typically employs a standalone computer 20 or the like as the data processing device, it is contemplated for some data processing involved in providing the immediate image label information checking (for example, computationally complex image analyses) to be implemented on a remote server (not shown) that is connected with the local electronic processing device 20 via a wired or wireless data communication connection. For example, the remote server may be a hospital server, cloud computing resource, or so forth connected with the local computer 20 via a hospital electronic network and/or the Internet. The display device 22 can be of any size, but to provide the apparatus 1 as a compact unit that can be conveniently positioned next to (or otherwise near to) the imaging device controller 4, the display 22 is typically relatively small, e.g. a 5-inch display, 10-inch display, 12-inch display, or so forth. In some embodiments, the apparatus 20 does not have any user input devices (i.e., nothing analogous to the keyboard, mouse, or other user input device 10 of the imaging device controller 4), although it is alternatively contemplated for the computer or other electronic processing device 20 to include a keyboard or the like for setting up the image label information checking software or for other purposes. The non-transitory storage medium 26 may, by way of non-limiting illustrative example, comprise one or more of a hard disk or other magnetic storage medium, a solid state drive (SSD), flash memory, or other electronic storage medium, an optical disk or other optical storage medium, various combinations thereof, and/or so forth.

In one example embodiment, both the apparatus 1 and the imaging device controller 4 can be operated by a single technologist in a single room. In another embodiment, both the apparatus 1 and the imaging device controller 4 can be operated by a single technologist in separate rooms. In another example, the apparatus 1 can be disposed in a remote location from the imaging device controller 4 and be operated by a single technologist, who can provide assistance to another technologist in the room housing the imaging device controller.

The electronic processing device 20 of the illustrative image label information checking apparatus 1 is operatively connected to receive a live video feed 17 of the display 6 of the imaging device controller 4. The live video feed 17 is, in the illustrative embodiment, provided by a video cable splitter 34 (e.g., a DVI splitter, a HDMI splitter, and so forth). In other embodiments, the live video feed 17 may be provided by a video cable connecting an auxiliary video output (e.g. aux vid out) port of the imaging device controller 4 to the electronic processing device 20 of the immediate DICOM label checker apparatus 1. This latter approach may be useful, for example, if the imaging device 2 is a compact ultrasound imaging device with an integral display, in which case it may not be convenient to connect a video cable splitter since the wiring of the display is in this case the wiring to the ultrasound display is entirely internal to the ultrasound imaging device cabinet—but, an "aux vid out" port may be provided in such a portable ultrasound imaging device. In another contemplated embodiment, screen-sharing software running on the imaging device controller 4 and the electronic processing device 20 provides the live video feed 17 to the electronic processing device 20. These are merely illustrative examples. Moreover, in alternative embodiments in which the image label information checker is implemented in the imaging device controller 4, there is no need for the live video feed extraction as the preview image is directly available to the imaging device controller 4.

The final clinical images are saved to the PACS 14 with image label information labeled thereto, typically in the form of DICOM labels or tags. As used herein, the term "image label information" (and variants thereof) refers to information extracted from the live video feed 17 of the imaging device controller 4 indicating a DICOM label of the clinical image (which may or may not yet be acquired). The image label information does not label the preview image 12, as the preview image is not saved to the PACS 14. In addition, the image label information does not constitute actual DICOM labels or tags with which the clinical image is (or will be) labeled.

The non-transitory storage medium 26 of the immediate DICOM label checker apparatus 1 stores instructions which are readable and executable by the at least one electronic processor 24 of the apparatus 1 (which as previously noted, is contemplated to include a remote server or servers on a local area network or the Internet) to perform disclosed operations including performing a method or process 100 for providing immediate checking of image label information for an imaging technician during an imaging examination. The checking method or process 100 includes a preview image extractor method or (sub-)process 36, and one or more image analyses 38, In some embodiments, the at least one electronic processor 20 of the workstation 12 is programmed to implement at least one machine-learning ML component 40 (e.g., one or more convolutional neural networks (CNNs) to extract the preview image 12 from the tapped live video feed 17. In some examples, the method 100 may be performed at least in part by cloud processing.

Figure 2:
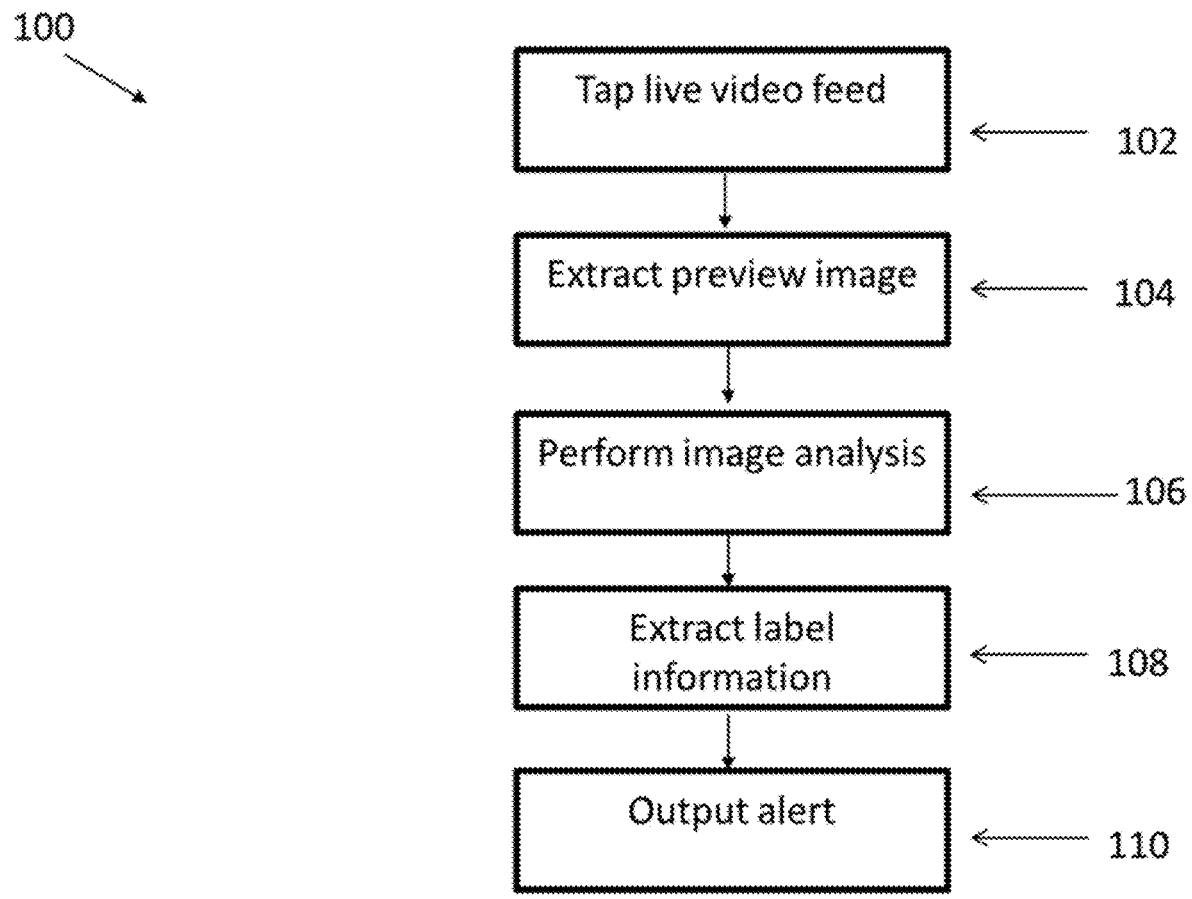
FIG. 2 shows example flowchart operations performed by the apparatus of FIG. 1.

With reference to FIG. 2, and with continuing reference to FIG. 1, an illustrative embodiment of the method 100 is diagrammatically shown as a flowchart. The method 100 is performed over the course of a medical imaging examination performed using the medical imaging device 2. At an operation 102, the electronic processing device 20 is programmed to receive the live video feed 17 of the imaging device controller 10 of the medical imaging device 2, e.g. via the video cable splitter 34.

At an operation 104, the electronic processing device 20 is programmed to extract the preview image 12 from the received live video feed 17. The extracted preview image 12 is displayed in the preview image viewport 9. To do so, the at least one electronic processor 20 in some embodiments is programmed to determine at least one of a modality of the imaging device 2 and/or an anatomy of a patient being imaged by the imaging device. For example, an OCR process can be performed on the live video feed 17 to relevant text identifying the modality and/or the anatomy. In another example, an image matching process can be performed on the live video feed 17 to graphical elements identifying the modality and/or the anatomy.

Based on the determined modality or imaged anatomy part, and/or attributes of the preview image displayed in the viewport (such as, for example, an identified rectangular border region), video frames from the tapped live video feed 17 are analyzed to detect the video frame containing the preview image 12. To do so, the at least one trained ML component (e.g., CNN) 40 is applied to the tapped live video feed 17 to detect and extract the preview image 12. In one example, the CNN 40 is configured to detect the preview image 12 by identifying, in the tapped live video feed 17, at least one of: a rectangular gray scale region with a dark boundary, size characteristics of a preview image, and location characteristics of a preview image.

At an operation 106, the electronic processing device 20 is programmed to perform an image analysis 38 on the extracted preview image 12 to generate preview-derived image label information. To do so, the at least one trained ML component 40 is applied to the extracted preview image 12 to generate the preview-derived image label information. (In alternative embodiments implemented in the imaging device controller 4, the operation 106 suitably operates on the preview image which is directly available at the imaging device controller 4, in which case the operations 102, 104 are suitably omitted.)

At an operation 108, the electronic processing device 20 is programmed to extract GUI-derived label information from the live video feed 17 of the GUI 8 excluding (or otherwise not including) the preview image 12 is displayed in the preview image viewport 9. (In alternative embodiments implemented in the imaging device controller 4, the operation 108 suitably operates directly information entered into and/or displayed on the GUI 8 without resort to a video feed, as this information is directly available at the imaging device controller 4.) The operation 108 can be performed in a variety of manners. In one example, the electronic processing device 20 is programmed to perform the image analysis 38 to identify a body part imaged by the extracted preview image 12. The GUI-derived image label information includes information related to the identified body part. In another example, the electronic processing device 20 is programmed to perform the image analysis 38 to identify an anatomical orientation of a body part imaged by the extracted preview image 12. The GUI-derived image label information includes information related to the identified anatomical orientation. In a further example, the electronic processing device 20 is programmed to perform an OCR process on the live video feed 17 to generate OCR text. At least a portion of the GUI-derived image label information can be determined based on the generated OCR text. In yet another example, the electronic processing device 20 is programmed to detect a user input, via the at least one user input device 10, captured by the live video feed 17 of the GUI 8. The user input can be indicative of a selection of a DICOM label. At least a portion of the GUI-derived image label information can be determined based on the detected user input. In another example, the electronic processing device 20 is programmed to detect a GUI symbol or icon displayed by the GUI 8 in the live video feed 17 of the GUI. In a further example, the electronic processing device 20 is programmed to match the live video feed 17 of the GUI 8 with a GUI template screen 42 (which can be stored in, and retrieved from, the non-transitory computer readable medium 26). The GUI template screen 42 contain information that can be typically included in the GUI 8. At least a portion of the GUI-derived image label information can be determined based on the matched GUI template screen 42. These are merely non-limiting examples, and should not be construed as limiting.

The operation 108 extracts GUI-derived image label information from the GUI excluding the preview image displayed in the preview image viewport. This reflects the approach in which the operation 106 performs image analysis on the preview image to generate preview-derived image label information. However, the operation 108 may in some embodiments extract GUI-derived image label information from content of the GUI shown in the preview image viewport other than the preview image itself. For example, the GUI may superimpose text labels on the preview image displayed in the preview image viewport, and the operation 108 may extract GUI-derived image label information from these superimposed text labels in the preview image viewport. Said another way, the exclusion of the preview image displayed in the preview image viewport from the analysis of operation 108 relates only to exclusion of the preview image itself, and does not exclude using (other) GUI content that might be shown in that viewport.

The use of the video feed 17 as the information source in the illustrative embodiment advantageously enables the apparatus 1 to be used in conjunction with numerous different modalities/imaged anatomies, and without modifying the imaging device controller 4.

The image label information can include information from which DICOM labels or header fields are generated, such as "ViewPosition", "ImageLaterality", "PatientOrientation", "BodyPartExamined", among numerous other DICOM labels. Hence, the apparatus 1 can be considered to be checking the DICOM labels, although what is actually checked is the image label information that is input to and/or displayed by the GUI 8, from which the DICOM labels are created. Moreover, what the apparatus 1 detects is an inconsistency between the preview-derived image label information and the GUI-derived image label information. Given an alert indicating such an inconsistency, the imaging technician can then review the situation to determine whether it is the preview image that is incorrect, or whether it is the GUI-derived image label information that is incorrect.

In one example, the detected modality can be mammography, in which the checked DICOM labels can include an analysis of "ViewPosition" (e.g., a cranio-caudal (CC) image, a medial-lateral-oblique (MLO) image, or special views such as spot compression); an analysis of laterality of the breast tissue; an analysis of a specific body part (e.g., to distinguish breast tissue from phantoms). In another example the detected modality can be radiography, and the detected anatomy is a chest, in which the checked DICOM labels can include an analysis of "ViewPosition" (e.g. an anterior-posterior view; a posterior-anterior view; a lateral view; and so forth). In a further view, the apparatus 1 can be used in orthopedic applications, including an analysis of DICOM header fields including "BodyPart"; "ViewPosition"; and "Laterality." More generally, in one example the image analysis 38 is operative to identify a body part imaged by the preview image 12, and the GUI-derived image label information includes body part information, and any inconsistency between the two differently derived image label information relating to body part imaged is detected. In another more general example, the image analysis 38 is operative to identify an anatomical orientation of a body part imaged by the preview image 12, and the GUI-derived image label information includes anatomical orientation information, and any inconsistency between the two differently derived image label information relating to anatomical orientation is detected. These are merely non-limiting examples. In an alternative approach, if the apparatus 1 is designed to work with only a specific imaging modality then there is no need to determine the modality, and this aspect of operations 104-108 can be omitted. Likewise, if the apparatus 1 is designed to work with only a specific imaged anatomy (e.g., in the case of a dedicated mammography imaging system, the anatomy is a breast) then there is no need to determine the imaged anatomy, and this aspect of operations 104-108 can be omitted.

At an operation 110, the electronic processing device 20 is programmed to output the alert 30 when the preview-derived image label information and the GUI-derived image label information are not consistent (e.g., do not match).

The alert 30 is output to indicate that the preview-derived image label information and the GUI-derived image label information do not match. The alert 30 can be any suitable alert, including, for example, a textual alert on the display device 6 of the imaging device controller 4 or the display device 22 of the apparatus 1, an audible alarm via the loudspeaker 28, graphical annotations on the extracted preview image displayed on the display 22, and so forth. In one example, the preview image 12 can be displayed with superimposed graphical annotations (comprising the alert 30) can be displayed on the display device 22. In another example, at least one frame of the video feed 17 of the GUI 8 can be displayed with superimposed annotations (comprising the alert 30) identifying the inconsistency of the preview-derived image label information and the GUI-derived image label information. Alternatively, the mismatched labels can be automatically corrected and sent to the PACS 14 after confirmation by the technologist.

In addition, once to the alert 30 is output, one or more additional steps can be performed. For example, the types of frequency of errors represented in the alert 30 can be logged, a corrective action taken can be logged, and trend analysis can be performed by the electronic processing device 20 to determine frequent errors (either department wide or user based) to determine potential training recommendations.

After the mismatched labels are corrected, a verification can be performed to ensure that the DICOM labels and tags are current. Advantageously, the verification algorithms to apply can be chosen based on, for example, a verified imaging protocol based on the immediate checking of image label information provided by the method 100. For example, a quality-based algorithm can be initiated by the electronic processing device 20 based on the confirmed (i.e., via a DICOM quality check) imaging protocol. For example, protocol-specific patient set up issues can be checked (e.g. ensuring the patient's eyes are out of x-ray fields if the imaged anatomy is proximate to the head, taking into account metal artifacts that may credibly be present in the imaged anatomy, scan length appropriate for the verified imaging protocol, and so forth) or image quality (e.g. metal artifacts, truncation, blurring from motion, or other artifacts (streaking from charge build up on ECG leads, etc.) are appropriate for the verified imaging protocol. Advantageously, this can improve both accuracy and efficiency by ensuring that the correct checks are performed for the verified imaging protocol and avoiding performing checks that are irrelevant or unnecessary for the verified imaging protocol.

In some embodiments, the final images stored in the PACS 14 can be labeled as having the DICOM labels corrected (e.g., the images that have had an alert 30 output for mismatched DICOM labels). Advantageously, this can improve searching for previous or similar cases by a medical professional. Additionally, the types and frequencies of corrections can be stored for later statistical analyses, and can be used in reporting quality checks to regulators and/or hospital administration. If, for example, a particular type of error is being made frequently this can trigger remedial training of imaging technicians. Such training may in some instances be targeted to a specific imaging technician who may be making excessive numbers of mistakes.

Figure 3:
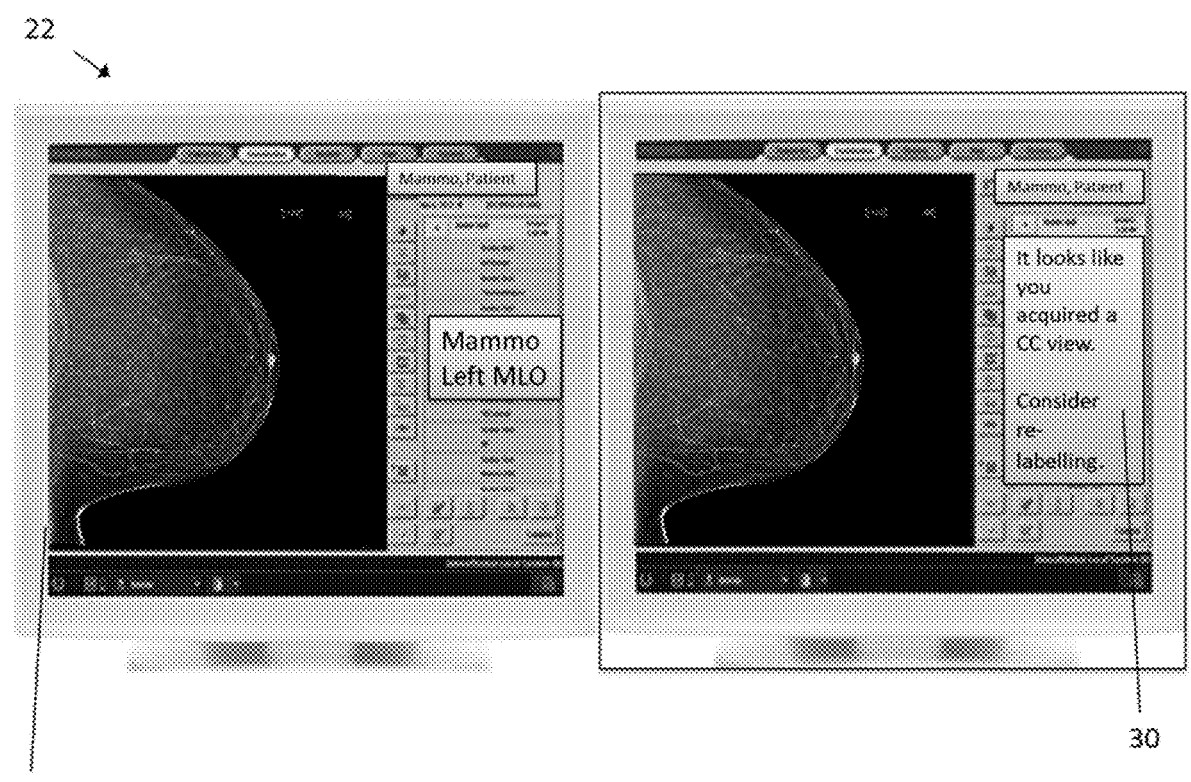
FIG. 3 shows an example of alerts displayed on the apparatus of FIG. 1.

FIG. 3 shows an example of the alert 30 as shown on the display device 22 (or the display 6). As shown in FIG. 3, the alert 30 can be textual messages (e.g., "it looks like you acquired a CC view" when the image is labeled as a MLO view; and so forth). In addition, the alert 30 can include advice for the technologist to resolve the issues (e.g., "consider re-labeling").

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. An apparatus for use in conjunction with a medical imaging device having an imaging device controller that displays a graphical user interface (GUI) including a preview image viewport, the apparatus comprising at least one electronic processor programmed to:
   acquire a preview image;
   perform an image analysis on a preview image displayed in the preview image viewport;
   apply at least one trained machine-learning component to the preview image to generate preview-derived image label information;
   acquire a clinical image having a higher resolution than the preview image;
   extract GUI-derived image label information from the clinical image, excluding the preview image displayed in the preview image viewport; and
   prior to storing the clinical image with image label information into a Picture Archiving and Communication System (PACS), output an alert when the preview-derived image label information and the GUI-derived image label information are not consistent, wherein the at least one electronic processor is programmed to label images acquired by the medical imaging device for which the alert has been output.

2. The apparatus of claim 1, wherein the image analysis is operative to identify a body part imaged by the preview image, and the GUI-derived image label information includes body part information.

3. The apparatus of claim 1, wherein the image analysis is operative to identify an anatomical orientation of a body part imaged by the preview image, and the GUI-derived image label information includes anatomical orientation information.

4. The apparatus of claim 1, wherein the at least one electronic processor is programmed to:
   receive a video feed of the GUI displayed on the imaging device controller; and
   extract the preview image displayed in the preview image viewport from the live video feed of the GUI;
   wherein the extraction of the GUI-derived image label information includes extracting the GUI-derived image label information from the live video feed of the GUI excluding the preview image displayed in the preview image viewport.

5. The apparatus of claim 4, wherein the at least one electronic processor is programmed to extract the GUI-derived image label information by operations including:
   performing optical character recognition (OCR) on the live video feed of the GUI to generate OCR text; and
   determining at least a portion of the GUI-derived image label information based on the OCR text.

6. The apparatus of claim 4, wherein the at least one electronic processor is programmed to extract the GUI-derived image label information by operations including:
   detecting a user input to the GUI captured by the live video feed of the GUI; and
   determining at least a portion of the GUI-derived image label information based on the detected user input.

7. The apparatus of claim 4, wherein the at least one electronic processor is programmed to extract the GUI-derived image label information by operations including:
   detecting a GUI symbol or icon displayed by the GUI in the live video feed of the GUI.

8. The apparatus of claim 4, wherein the at least one electronic processor is programmed to extract the GUI-derived image label information by operations including:
   matching the live video feed of the GUI with a GUI template screen; and
   determining at least a portion of the GUI-derived image label information based on the matched GUI template screen.

9. The apparatus of claim 8, wherein the at least one electronic processor is programmed to output the alert by:
   displaying, on at least one display device that is separate from the imaging device controller, at least one frame of the video feed of the GUI with superimposed annotations identifying the inconsistency of the preview-derived image label information and the GUI-derived image label information.

10. The apparatus of claim 4, further including:
    at least one display device separate from the imaging device controller, wherein the at least one electronic processor is programmed to output the alert on the display device that is separate from the imaging device controller.

11. The apparatus of claim 10, wherein the at least one electronic processor is programmed to output the alert by:
    displaying, on at least one display device that is separate from the imaging device controller, the preview image with superimposed graphical annotations.

12. The apparatus of claim 4, further including:
    a video cable splitter operatively connected with the imaging device controller via which the at least one electronic processor receives the video feed of the GUI displayed on the imaging device controller.

13. The apparatus of claim 4, further including at least one of:
    a video cable connecting an auxiliary video output port of the image device controller via which the at least one electronic processor receives the video feed of the GUI displayed on the imaging device controller; and
    screen-sharing software running on the imaging device controller and the electronic processing device, wherein the screen-sharing software provides the live video feed to the electronic processing device.

14. The apparatus of claim 1, wherein the at least one electronic processor is programmed to:

verify a protocol when the preview-derived image label information and the GUI-derived image label information are consistent;

wherein the protocol comprises one or more of protocol set up or image quality recommendations.

15. The apparatus of claim 1, wherein the at least one electronic processor is programmed to:

responsive to the alert being output, carry out at least one of (i) logging a frequency of error represented in the alert, (ii) logging a corrective action to address the alert, and (iii) performing a trend analysis to determine frequency of errors represented in the alert.

16. A computer-implemented method for providing checking of label information in a medical imaging device, the method comprising:

acquiring a preview image;

performing an image analysis on a preview image displayed in a preview image viewport;

applying at least one trained machine-learning component to the preview image to generate preview-derived image label information;

acquiring a clinical image having a higher resolution than the preview image;

extracting GUI-derived image label information from the clinical image, excluding the preview image displayed in the preview image viewport; and prior to storing the clinical image with image label information into a Picture Archiving and Communication System (PACS), outputting an alert when the preview-derived image label information and the GUI-derived image label information are not consistent, wherein at least one electronic processor is programmed to label images acquired by the medical imaging device for which the alert has been output.

17. The method of claim 16, further including outputting the alert by:

displaying the preview image with superimposed graphical annotations.

\* \* \* \* \*